United States Patent
Ichim et al.

(10) Patent No.: US 11,814,430 B2
(45) Date of Patent: Nov. 14, 2023

(54) INCREASING RESPONSES TO CHECKPOINT INHIBITORS BY EXTRACORPOREAL APHERESIS

(71) Applicant: IMMUNICOM, INC., San Diego, CA (US)

(72) Inventors: Thomas Emanuel Ichim, San Diego, CA (US); Steven Francis Josephs, San Diego, CA (US); Stephen Michael Prince, San Diego, CA (US); Amir Jafri, San Diego, CA (US); Robert Segal, San Dieog, CA (US); David L. Schlotterbeck, San Diego, CA (US)

(73) Assignee: IMMUNICOM, INC., San Diego, CA (US)

( * ) Notice: Subject to any disclaimer, the term of this patent is extended or adjusted under 35 U.S.C. 154(b) by 0 days.

(21) Appl. No.: 17/175,503

(22) Filed: Feb. 12, 2021

(65) Prior Publication Data

US 2021/0163597 A1    Jun. 3, 2021

Related U.S. Application Data

(63) Continuation of application No. PCT/US2019/031184, filed on May 7, 2019.

(51) Int. Cl.
| | |
|---|---|
| *C07K 16/28* | (2006.01) |
| *A61M 1/34* | (2006.01) |
| *A61M 1/36* | (2006.01) |

(52) U.S. Cl.
CPC ....... *C07K 16/2818* (2013.01); *A61M 1/3496* (2013.01); *A61M 1/3693* (2013.01); *C07K 16/2827* (2013.01); *A61M 2202/0415* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 7,854,717 | B1* | 12/2010 | Lentz | ........... A61P 35/00 604/4.01 |
| 10,918,737 | B2* | 2/2021 | Levade | ........... C07K 16/241 |
| 2005/0265996 | A1* | 12/2005 | Lentz | ........... A61M 1/3472 424/141.1 |

FOREIGN PATENT DOCUMENTS

WO    2005/003298 A2    1/2005

OTHER PUBLICATIONS

Almagro & Fransson, Frontiers in Bioscience 2008; 13:1619-33 (Year: 2008).*
Kent et al. (Drugs, 74:1993-2013, 2014) (Year: 2014).*
Perez-Ruiz et al. (Nature 569, 428-432 (2019) (Year: 2019).*
International Search Report dated Jan. 16, 2020 in PCT/US2019/031184 (4 pages).
International Written Opinion dated Jan. 16, 2020 in PCT/US2019/031184 (6 pages).
Nicholson et al., "A case for consideration by apheresis practitioners: Melanoma and PD-1 inhibitor treatment in a patient with multiple relapses of immune thrombotic thrombocytopenia purpura", Transfus Apher Sci. Apr. 2019;58(2):123-124. doi: 10.1016/j.transci.2019.03.001. (Abstract only).
Marhelava et al., "Targeting Negative and Positive Immune Checkpoints with Monoclonal Antibodies in Therapy of Cancer", Cancers (Basel). Nov. 8, 2019;11(11):1756. doi: 10.3390/cancers11111756.

* cited by examiner

*Primary Examiner* — Meera Natarajan
(74) *Attorney, Agent, or Firm* — PILLSBURY WINTHROP SHAW PITTMAN LLP

(57) ABSTRACT

The invention provides means, methods, and compositions of matter useful for enhancing tumor response to checkpoint inhibitors. In one embodiment, the invention teaches utilization of extracorporeal apheresis, specifically removal of various tumor derived, or tumor microenvironment derived immunological "blocking factors". In one embodiment the invention provides the removal of soluble TNF-alpha receptors (sTNF-Rs) as a means of augmenting efficacy of immune checkpoint inhibitors. In one specific embodiment removal of sTNF-Rs is utilized to enhance efficacy of inhibitors of the PD-1/PD-L1 pathway, and/or the CD28/CTLA-4 pathway.

11 Claims, No Drawings

INCREASING RESPONSES TO CHECKPOINT INHIBITORS BY EXTRACORPOREAL APHERESIS

BACKGROUND

There is an increasing prevalence of cancer in human and its significant contribution to mortality means there is a continuing need for new therapies. Elimination of the cancer, a reduction in its size, the disruption of its supporting vasculature, or reducing the number of cancer cells circulating in the blood or lymph systems are goals of current cancer therapies. Mechanistically, therapies for cancer are designed to combat tumors or cells metastasizing from tumors typically rely on a cytotoxic activity. That activity might be a cytotoxic effect an active agent has itself or it might be an effect employed indirectly by the active agent such as through the modulation of immune responses.

It is known that genetic and epigenetic changes occur in tissues as they transform to take on the phenotype of a cancer cell. Different steps in the malignant transformation process, including acquisition of the mutator phenotype, which is associated with loss of tumor suppressor activity, often results in the generation of neoantigens, which are subject to immune recognition.

Various attempts have been made to help the immune system to fight tumors. One early approach involved a general stimulation of the immune system through the administration of bacteria (live or killed) to elicit a general immune response which would also be directed against the tumor. Existing innate stimulators of immunity include BCG [1-10], lyophilized incubation mixture of group A Streptococcus pyogenes (OK-432) [11-26], CSF-470 [27, 28], as well as doses of chemotherapies that can selectively suppress Treg cells [29-39].

As far back as 1975 [40], it was known that administration of non-specific immune activators could induce local and in some cases systemic regression of cancer. For example, in one study, 6 patients with intradermal metastases of malignant melanoma were treated with intralesional BCG. Four patients showed a good response with regression of injected, and in some cases, uninjected lesions, whereas the other two developed metastatic visceral disease and died. Three of the six patients had complete regression of all lesions, and one exhibited complete regression of untreated lesions. All remain free of disease. The fourth patient had complete regression of injected and of some untreated lesions, but developed widespread dissemination and died. Three of four responders (i.e. those patients in whom treated lesions decreased in size by more than 50% for more than 1 month) showed a dramatic increase in lymphocyte stimulation to melanoma antigens. All responders (four out of four) had a marked increase to phytohemagglutinin (PHA), whereas non responders had no increase in lymphocyte stimulation either to melanoma antigens or PHA. These data suggested the other important point, which is that innate immune activation can lead to stimulation of antigen-specific T cell and B cell mediated immune responses. Recent approaches aimed at helping the immune system specifically to recognize tumor-specific antigens involve immunization with cancer-specific antigens, typically combined with an adjuvant (a substance which is known to cause or enhance an immune response) to the subject. Tumor specific antigens are well known and include the group of cancer testes antigens (CT antigens) or germ cell antigens that are reactivated in cancerous tissues. It is known that the usual lack of a powerful immune response to tumor associated antigens (TAAs) is due to a combination of factors. T cells have a key role in the immune response, which is mediated through antigen recognition by the T cell receptor (TCR), and they coordinate a balance between co-stimulatory and inhibitory signals known as immune checkpoints. These inhibitory signals function as natural suppressors of the immune system as an important mechanism for for maintenance of self-tolerance and to protect tissues from damage when the immune system is responding to pathogenic infection. However, disregulated immune suppression reduces what could otherwise be a helpful response by the body to avoid the development of tumors. Cytokines, other stimulatory molecules such as CpG (stimulating dendritic cells), Toll-like receptor ligands and other molecular adjuvants enhance the immune response. Co-stimulatory interactions involving T cells directly can be enhanced using agonistic antibodies to receptors including OX40, CD28, CD27 and CD137. Other immune system activating therapies include blocking and/or depleting inhibitory cells or molecules and include the use of antagonistic antibodies against what are known as immune checkpoints [41]. It is known that immune cells express proteins that are immune checkpoints that control and down-regulate the immune response. These are best defined in T lymphocytes and include PD-1, CTLA-4, TIM-3 and LAG3. Tumor cells express the ligands to these receptors. When T cells bind the ligand to these proteins on the tumor cells, the T cell is turned off and does not attempt to attack the tumor cell. Thus, checkpoint immune suppression is part of the complex strategy used by the tumor to evade the patient's immune system and Is responsible for resistance to immunotherapy. Biopharmaceutical companies have successfully developed therapeutic checkpoint inhibitors that block the receptor/ligand interaction to promote the adaptive immune response to the tumor. Six checkpoint inhibitors are currently approved, pembrolizumab, nivolumab, atezolizumab, avelumab, durvalumab, and ipilimumab for a wide variety of solid tumors including melanoma, lung, bladder, gastric cancers and others. T cells are central to the immune response to cancers and there is interest in the field in using tumor infiltrating lymphocytes (TILs) in the treatment and understanding of cancer. Through their T cell receptors (TCRs), T cells are reactive to specific antigens within a tumor. Tumor cells carry genetic mutations, many of which contribute directly or indirectly to malignancy. A mutation in an expressed sequence will typically result in a neoantigen, an antigen that is not known to the immune system and thus recognized as foreign and able to elicit an immune response. The importance of TIL is that they are associated with superior patient prognosis including in gastric cancer [42], breast cancer [43-46], melanoma [47], head and neck cancer [48], thus suggesting an active role of the immune system in contributing to cancer survival.

Unfortunately, despite the great advances in understanding of the immune-cancer interaction, and development of novel first in class drugs around this concept, many patients still do not respond to immunotherapies, and in some cases, those that respond suffer from relapse. The current invention teaches means of augmenting efficacy of immunotherapies, specifically of checkpoint inhibitors, by removal of tumor derived and/or tumor microenvironment derived immunological blocking factors using extracorporeal means.

SUMMARY

Embodiments herein are directed to methods of enhancing the efficacy of an immune checkpoint inhibitor administered to a patient suffering from a tumor comprising: identifying a patient suffering from a tumor; administering an immunological checkpoint inhibitor to said patient to treat said tumor or ameliorate the effects of said tumor; extracorporeally removing immunological blocking factors that inhibit the effectiveness of said immunological checkpoint inhibitor in an amount sufficient to augment the efficacy of said immunological checkpoint inhibitor in either treating or ameliorating the effects of said tumor, wherein said extracorporeal removal is conducted at a time selected from the group consisting of: before, concurrently, and subsequent to the administration of said immunological checkpoint inhibitor.

More specifically, disclosed herein are methods wherein said efficacy of said checkpoint inhibitor is based on an endpoint selected from the group consisting of: a) tumor regression; b) tumor stabilization; c) reduction in tumor growth; d) inhibition of metastasis; e) stabilization of metastasis; f) reduction of metastatic growth; g) encapsulation of tumor and/or metastasis; h) augmentation of cytokines associated with tumor inhibition; i) decrease in cytokines associated with tumor progression; j) suppression of angiogenesis; k) augmentation of tumor infiltrating lymphocytes; l) switch of intratumoral macrophages from M2 to M1 phenotype; m) augmentation of tumor infiltrating dendritic cells; n) augmentation of tumor infiltrating killer T-cells o) reduction of tumor associated T regulatory cells; and p) reduction in tumor associated myeloid suppressor cells.

According to further embodiments, said checkpoint inhibitor is an agent capable of suppressing activity of a molecule selected from the group consisting of: PD-1, PD-L1, CTLA-4, PD-L2, LAG3, Tim3, 2B4, A2aR, ID02, B7-H3, B7-H4, BTLA, CD2, CD20, CD27, CD28, CD30, CD33, CD40, CD52, CD70, CD112, CD137, CD160, CD226, CD276, DR3, OX-40, GALS, GITR, ICOS, HVEM, IDO1, KIR, LAIR, LIGHT, MARCO, PS, SLAM, TIGIT, VISTA, and VTCN1

According to other embodiments said immunological blocking factor is soluble TNF-alpha receptor.

According to further embodiments, disclosed herein are methods wherein said immunological blocking factor is selected from the group consisting of: a) soluble HLA-G; b) soluble MICA; c) interleukin-10; d) interleukin-20; e) VEGF; f) soluble IL-2 receptor; g) soluble IL-15 receptor; h) interleukin-35 and i) soluble interferon gamma receptor.

According to more specific embodiments, said removal of soluble TNF-alpha receptor is performed by affinity capture to TNF-alpha trimers.

According to further embodiments said checkpoint inhibitor is administered via a route selected from the group consisting of: intravenously, intramuscularly, parenterally, nasally, intratumorally, intraosseously, subcutaneously, sublingually, intrarectally, intrathecally, intraventricularly, orally, intraocularly, topically, or via inhalation, nanocell and/or nanobubble injection.

According to more specific embodiments, the immunological checkpoint inhibitor is selected from the group consisting of PD-1, PD-L1, and CTLA-4.

According to other embodiments, the inhibitor of PD-1 is an anti-PD-1 antibody selected from the group consisting of nivolumab and pembrolizumab.

Further embodiment are directed to methods wherein the inhibitor of PD-L1 is anti-PD-L1 antibody selected from the group consisting of: BMS-936559, durvalumab, atezolizumab, avelumab, MPDL3280A, MEDI4736, MSB0010718C, and MDX1105-01.

According to other embodiments, the inhibitor of CTLA-4 is an anti-CTLA-4 antibody selected from the group consisting of ipilimumab and tremelimumab.

According to certain embodiments, said removal of said soluble TNF-alpha receptor is performed using an extracorporeal affinity capture substrate comprising immobilized TNF-alpha molecules selected from the group consisting of: TNF-alpha trimers, native TNF-alpha molecules, and mutated forms of TNF-alpha, wherein said immobilized TNF-alpha molecules on the extracorporeal affinity capture substrate have at least one binding site capable of selectively binding to soluble TNF alpha receptor from a biological fluid.

Further methods include embodiments wherein said removal of immunological blocking factors is performed using an apheresis system utilizing centrifugal plasma separation.

Additional methods include embodiments, wherein said removal of immunological blocking factors is performed using an apheresis system utilizing membrane plasma separation.

Other aspects embody methods wherein enhancing efficacy of an immune checkpoint inhibitor is accomplished by performing one or more clinical procedures involving the removal of tumor derived blocking factors to prepare and/or condition the patient.

Still further embodiments include methods wherein said removal of soluble TNF-alpha receptor is performed by affinity capture to TNF-alpha trimers.

According to more specific embodiments said checkpoint inhibitor is administered intravenously, intramuscularly, parenterally, nasally, intratumorally, intraosseously, subcutaneously, sublingually, intrarectally, intrathecally, intraventricularly, orally, topically, or via inhalation, nanocell and/or nanobubble injection.

According to further embodiments said extracorporeal removal of immune blocking factors primes antigen presenting cells for enhanced ability to produce interleukin-12 subsequent to administration of a checkpoint inhibitor.

Further embodiments are directed to an immune checkpoint inhibitor for use in a method of treating a tumor in a patient, the method comprising: identifying a patient suffering from a tumor; administering an immunological checkpoint inhibitor to said patient to treat said tumor or ameliorate the effects of said tumor; and extracorporeally removing immunological blocking factors that inhibit the effectiveness of said immunological checkpoint inhibitor, wherein said extracorporeal removal is conducted at a time selected from the group consisting of: before, concurrently, and subsequent to the administration of said immunological checkpoint inhibitor. All methods disclosed herein can be used with said immune checkpoint inhibitors.

DESCRIPTION OF THE INVENTION

The invention discloses means of augmenting therapeutic ability of immunological checkpoint inhibitors by removal of immunological blocking factors through extracorporeal means. In one embodiment, the invention relates to the field of cancer therapy, specifically means of augmenting efficacy of cancer therapy. In particular, the invention provides methods of generating T cell populations capable of promoting the suppression of cancer, as well as directly killing the cancer. As used herein, the term "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, and diminishment of any direct or indirect pathological consequences of the disease, preventing metastasis, lowering the rate of disease progression, amelioration or palliation of the disease state, and inducing remission or improving prognosis.

The term "extracorporeal means" is defined as the use of an extracorporeal device or system through which blood or blood constituents obtained from a patient are passed through a device for the removal of the immune inhibitor(s) and wherein the blood or blood constituents that are depleted of immune inhibitor(s) are reinfused into the patient. The extracorporeal device is comprised of materials that selectively binds to and captures the specified inhibitor(s) to prevent them from being reinfused into the patient.

The term "affinity capture" means the selective binding of a specific substance or molecule by a chemical attraction.

The term "affinity capture substrate" means a material comprising an affinity capture molecule.

The term "antibody" includes therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tocilizumab, tositumomab, trastuzumab, tucotuzumab, ublituximab, veltuzumab, vorsetuzumab, votumumab, zalutumumab, CC49 and 3F8. In some embodiments the invention teaches the combination use of extracorporeal removal of blocking factors as a means of augmenting therapeutic efficacy of the mentioned antibodies. In other embodiments the combination of antibodies, together with extracorporeal removal of blocking factors, is further combined with administration of checkpoint inhibitors. The invention is particularly of importance to therapeutic antibodies whose actions are mediated by antibody dependent cellular toxicity. The mentioned antibodies can be utilized individually or in combination. Furthermore administration of other immune modulators is envisioned within the scope of the invention. Immune modulators may be activators of innate immunity such as toll like receptor agonists. Other immune modulators stimulate adaptive immunity such as T and B cells. Furthermore, immune stimulation by be achieved by removal of immune suppressive cells utilizing approaches that deplete myeloid derived suppressor cells, Th3 cells, T regulatory cells, type 2 neutrophils, type 2 macrophages and eosinophils.

The terms "antigen-presenting cell (s)", "APC" or "APCs" include both intact, whole cells as well as other molecules (all of allogeneic origin) which are capable of inducing the presentation of one or more antigens, preferably in association with class I MHC molecules, and all types of mononuclear cells which are capable of inducing an allogeneic immune response. Preferably whole viable cells are used as APCs. Examples of suitable APCs are, but not limited to, whole cells such as monocytes, macrophages, DCs, monocyte-derived DCs, macrophage-derived DCs, B cells and myeloid leukemia cells e. g. cell lines THP-1, U937, HL-60 or CEM-CM3. Myeloid leukemia cells are said to provide so called pre-monocytes. In some embodiments of the invention, tumor induced immaturity of antigen presenting cells is overcome by extracorporeal removal of tumor associated blocking factors. Said removal results in a predisposition of antigen presenting cells to mature in response to administration of checkpoint inhibitors.

The terms "cancer", "neoplasm" and "tumor" are used interchangeably and in either the singular or plural form, as appearing in the present specification and claims, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e. g. by such procedures as CAT scan, magnetic resonance imaging (MRI), X-ray, ultrasound or palpation. Non-limiting examples of tumors/cancers relevant for the present invention are carcinomas (e.g. breast cancer, prostate cancer, lung cancer, colorectal cancer, renal cancer, gastric cancer and pancreatic cancer), sarcomas (e.g. bone cancer and synovial cancer), neuro-endocrine tumors (e.g. glioblastoma, medulloblastoma and neuroblastoma), leukemias, lymphomas and squamous cell cancer (e.g. cervical cancer, vaginal cancer and oral cancer). Further, non-limiting examples of tumors/cancers relevant for the present invention are, glioma, fibroblastoma, neurosarcoma, uterine cancer, melanoma, testicular tumors, astrocytoma, ectopic hormone-producing tumor, ovarian cancer, bladder cancer, Wilm's tumor, vasoactive intestinal peptide secreting tumors, head and neck squamous cell cancer, esophageal cancer, or metastatic cancer. Prostate cancer and breast cancer are particularly preferred.

For the practice of the invention, the term "chemotherapy" is meant to encompass any non-proteinaceous (i.e, non-peptidic) chemical compound useful in the treatment of cancer. Examples of chemotherapeutic agents include reactive oxygen agents such as artimesinin and alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin;

duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiII, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (Adramycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK; razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL®, Bristol Meyers Squibb Oncology, Princeton, N.J.) and docetaxel (TAXOTERE®, Rhone-Poulenc Rorer, Antony, France); chlorambucil; gemcitabine (GEMZAR®); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; FOLFIRI (fluorouracil, leucovorin, and irinotecan) and pharmaceutically acceptable salts, acids or derivatives of any of the above. In some embodiments the efficacy of chemotherapy is augmented by utilization of extracorporeal removal of blocking factors. Furthermore, combination of the mentioned chemotherapies may be utilized together with checkpoint inhibitors. The invention is particularly relevant in situations where efficacy of chemotherapy is related to immunological activity.

The terms "extracorporeal system" and "extracorporeal removal" refer to one or methods for depleting concentrations of substances from whole blood and/or plasma, wherein said substances are immune suppressive. Methods for depleting substances from plasma can utilize systems that perform plasma separation using centrifugal force or separation via membrane, including but not limited to tangential flow systems and/or capillary means. In one embodiment, said extracorporeal means is a single-chain TNF-alpha based affinity column, termed the "LW-02" device, which may be used in combination with the Terumo Optia apheresis system.

The term "myeloid suppressor cell" is equivalent to immature myeloid progenitor cells, myeloid derived suppressor cells, natural suppressor cells, or immature neutrophil/monocyte precursors.

The terms "vaccine", "immunogen", or immunogenic composition" are used herein to refer to a compound or composition that is capable of conferring a degree of specific immunity when administered to a human or animal subject. As used in this disclosure, a "cellular vaccine" or "cellular immunogen" refers to a composition comprising at least one cell population, which is optionally inactivated, as an active ingredient. The immunogens, and immunogenic compositions of this invention are active, which mean that they are capable of stimulating a specific immunological response (such as an anti-tumor antigen or anti-cancer cell response) mediated at least in part by the immune system of the host. The immunological response may comprise antibodies, immunoreactive cells (such as helper/inducer or cytotoxic cells), or any combination thereof, and is preferably directed towards an antigen that is present on a tumor towards which the treatment is directed. The response may be elicited or re-stimulated in a subject by administration of either single or multiple doses. A compound or composition is "immunogenic" if it is capable of either: a) generating an immune response against an antigen (such as a tumor antigen) in a naive individual; or b) reconstituting, boosting, or maintaining an immune response in an individual beyond what would occur if the compound or composition was not administered. A composition is immunogenic if it is capable of attaining either of these criteria when administered in single or multiple doses.

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12 amino acids or even longer, and in case of MHC class II peptides (e.g. elongated variants of the peptides of the invention) they can be as long as 15, 16, 17, 18, 19, 20 or 23 or more amino acids in length. Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo. The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The human in need thereof may be an individual who has or is suspected of having a cancer. In some of variations, the human is at risk of developing a cancer (e.g., a human who is genetically or otherwise predisposed to developing a cancer) and who has or has not been diagnosed with the cancer. As used herein, an "at risk" subject is a subject who is at risk of developing cancer (e.g., a hematologic malignancy). The subject may or may not have detectable disease, and may or may not have displayed detectable disease prior to the treatment methods described herein. An at-risk subject may have one or more so-called risk factors, which are measurable parameters that correlate with development of cancer, such as described herein. A subject having one or more of these risk factors has a higher probability of developing cancer than an individual without these risk factor(s). These risk factors may include, for example, age, sex, race, diet, history of previous disease, presence of precursor disease, genetic (e.g., hereditary) considerations, and environmental exposure. In some embodiments, a human at risk for cancer includes, for example, a human whose relatives have experienced this disease, and those whose risk is determined by analysis of genetic or biochemical markers. Prior history of having cancer may also be a risk factor for instances of cancer recurrence. In some embodiments, provided herein is a method for treating a human who exhibits one or more symptoms associated with cancer (e.g., a hematologic malignancy). In some embodiments, the human is at an early stage of cancer. In other embodiments, the human is at an advanced stage of cancer.

Overall survival (OS) is defined as the time elapsed from start of treatment until death of any cause. Progression Free Survival (PFS) (RECIST 1.1) is calculated from start of treatment until disease progression or death. Objective response rate [CR (Complete Response) or PR (Partial Response) or SD (Stable Disease)] is defined as the percent of patients with best confirmed response CR or PR or SD, using CT or MRI, and determined by a central reader per RECIST 1.1. The response must be confirmed by a subsequent determination greater than or equal to 4 weeks apart. In some instances PET is used. The evaluations and measurements are performed at screening, then at 8-week intervals starting from first treatment until PD (Progressive Disease) or initiation of another or additional anti-tumor therapy, whichever occurs first. In addition, scans are performed at each long-term follow-up visit until progression.

In one embodiment of the invention patients are chosen in which a high degree of cancer associated immune suppression present. Immune suppression is assessed using different means known in the art and can include quantification of number of immune cells in circulation, quantification of activity of immune cells in circulation, quantification of the number of immune cells found intratumorally, quantification of activity of immune cells found intratumorally, quantification of the number of immune cells found peritumorally, and quantification of activity of immune cells found peritumorally. In some embodiments of the invention, quantification of immune cells comprises identification and assessment of activity of cells possessing tumor cytolytic and/or tumor inhibitory activity, such cells include natural killer cells (NK), gamma delta T cells, natural killer T cells (NKT), innate lymphoid cells, cytotoxic T lymphocytes (CTL), and helper T cells (Th). Activities of immune cells could be ability to stimulate other immune cells, killing activity, tumor-growth inhibitory activity, as well as suppression of angiogenesis. Other means of assessing suppression of immunity includes quantification of immune suppressive cells. For example, elevations in immature dendritic cells, Th2 cells, Th3 cells, myeloid suppressor cells, M2 macrophages, T regulatory cells, N2 neutrophils, and infiltration by mesenchymal stem cells possessing immune suppressive properties, are all measurements for selecting patients with immune suppression.

In some embodiments, extracorporeal removal of blocking factors is utilized to reduce the immune modulatory activity of myeloid suppressor cells as a means of inducing immunological activation. Myeloid suppressor cells are believed to be similar to the "natural suppressor" cells described by the Singhal group in the 1970s. Natural suppressor cells were found to be bone marrow derived cells possessing ability to antigen-nonspecifically suppress T cell proliferation after immune activation [49-55], and are upregulated by cancer and pregnancy [56-63]. These properties are similar to the currently described properties of myeloid derived suppressor cells [64].

In some embodiments of the invention, vitamin D3 is added to extracorporeal removal of blocking factors in order to augment differentiation and/or loss of immune suppressive ability of said myeloid derived suppressor cells. Utilization of vitamin D3 to reduce cancer associated immune suppression is described in this publication and incorporated by reference [65, 66].

The invention teaches that in patients with pre-existing immune suppression, removal of extracorporeal blocking factors may be used to increase efficacy of checkpoint inhibitor drugs. For the practice of the invention, various checkpoint inhibitors may be utilized together with extracorporeal removal of immunological blocking factors for enhanced therapeutic activity. Examples of such checkpoint inhibitors include: a) Inhibitors of Programmed Death 1 (PD-1, CD279), such as nivolumab (OPDIVO®, BMS-936558, MDX1106, or MK-34775), and pembrolizumab (KEYTRUDA®, MK-3475, SCH-900475, lambrolizumab, CAS Reg. No. 1374853-91-4), as well as the PD-1 blocking agents described in U.S. Pat. Nos. 7,488,802, 7,943,743, 8,008,449, 8,168,757, 8,217,149, WO 03042402, WO 2008156712, WO 2010089411, WO 2010036959, WO 2011066342, WO 2011159877, WO 2011082400, and WO 2011161699; b) Inhibitors of Programmed Death—Ligand 1 (PD-L1, also known as B7-H1 and CD274), including antibodies such as BMS-936559, MPDL3280A), MEDI4736, MSB0010718C, and MDX1105-01); also including: atezolizumab, durvalumab and avelumab; c) Inhibitors of CTLA-4, such as ipilimumab (YERVOY®, MDX-010, BMS-734016, and MDX-101), tremelimumab, antibody clone BNI3 (Abcam), RNA inhibitors, including those described in WO 1999/032619, WO 2001/029058, U.S. 2003/0051263, U.S. 2003/0055020, U.S. 2003/0056235, U.S. 2004/265839, U.S. 2005/0100913, U.S.

2006/0024798, U.S. 2008/0050342, U.S. 2008/0081373, U.S. 2008/0248576, U.S. 2008/055443, U.S. Pat. Nos. 6,506,559, 7,282,564, 7,538,095 and 7,560,438 (each incorporated herein by reference); d) Inhibitors of PD-L2 (B7-DC, CD273), such as AMP-224 (Amplimune, Inc.) and rHIgM12B7; and e) Inhibitors of checkpoint proteins, including: LAG3, such as IMP321; TIM3 (HAVCR2); 2B4; A2aR, ID02; B7H1; B7-H3 or B7H3, such as antibody MGA271; B7H4; BTLA; CD2; CD20, such as ibritumomab tiuxetan, ofatumumab, rituximab, obinutuzumab and tositumomab; CD27, such as CDX-1127; CD28; CD30, such as brentuximab vedotin; CD33, such as gemtuzumab ozogamicin; CD40; CD52, such as alemtuzumab; CD70; CD80; CD86; CD112; CD137; CD160; CD226; CD276; DR3; OX-40 (TNFRSF.sub.4 and CD134); GALS; GITR; such as TRX518; HAVCR2; HVEM; IDO1; ICOS (inducible T cell costimulator; CD278); such as MEDI570 (MedImmune LLC) and AMG557 (Amgen); KIR; LAIR; LIGHT; MARCO (macrophage receptor with collageneous structure); PS (phosphatidylserine); SLAM; TIGIT; VISTA; and VTCN1; or a combinations thereof. In another variation, the checkpoint inhibitor is an inhibitor of a checkpoint protein selected from the group of PD-1, PD-L1, and CTLA-4. In another variation, the checkpoint inhibitor is selected from the group of an anti-PD-1 antibody, and anti-PD-L1 antibody, and an anti-CTLA-4 antibody. In one variation, the anti-PD-1 antibody is selected from the group of nivolumab, pembrolizumab, and lambrolizumab. In another variation, the anti-PD-L1 antibody is selected from the group of as BMS-936559, MPDL3280A, MEDI4736, MSB0010718C, and MDX1105-01. In yet other variations, the anti-PD-L1 antibody is selected from the group of durvalumab, atezolizumab, and avelumab. In another variation, the anti-CTLA-4 antibody is selected from the group of ipilimumab and tremelimumab. In one embodiment, the check point inhibitor is selected from the group consisting of nivolumab, pembrolizumab, lambrolizumab, BMS-936559, MPDL3280A, MEDI4736, MSB0010718C, MDX1105-01, durvalumab, atezolizumab, avelumab, ipilimumab, and tremelimumab. In certain embodiment, the check point inhibitor is selected from the group consisting of nivolumab, pembrolizumab, lambrolizumab, durvalumab, atezolizumab, avelumab, ipilimumab, and tremelimumab. In one embodiment, the check point inhibitor is selected from the group consisting of nivolumab, pembrolizumab, durvalumab, atezolizumab, and avelumab. Said checkpoint inhibitors listed may be administered via multiple methods, including but not limited intravenously, intramuscularly, parenterally, nasally, intratumorally, intraosseously, subcutaneously, sublingually, intrarectally, intrathecally, intraventricularly, orally, intra-ocular, topically, or via inhalation, nanocell and/or nanobubble injection. For practices of the invention, the enhancement of efficacy of an immune checkpoint inhibitor may be accomplished by performing one or more clinical procedures involving the removal of tumor derived blocking factors to prepare and/or condition the patient. Said removal may be performed at various time points prior to administration of said checkpoint inhibitor(s). The determination of time points of removal, in some embodiments, is performed based on immunological and/or oncological assessment of the patient. In some situations, immune activity of the patient is assessed, and used as a basis for determining the amount and frequency of extracorporeal treatments prior to administration of checkpoint inhibitors. In some situations, it may be desirable to continue extracorporeal treatments while administering checkpoint inhibitors. Furthermore, in some situations it may be desirable to continue extracorporeal treatment following administration of checkpoint inhibitors.

In some embodiments, checkpoint inhibitor drugs are increased in efficacy by removal of extracorporeal blocking factors. Said checkpoint inhibitor may be used to further increase in efficacy by addition of one or more cancer vaccines, which is referred to as "active immunization". In some embodiments of the invention, administration of checkpoint inhibitors is performed together with active immunization. Immunization may take the form of peptides, proteins, altered peptide ligands, and cell therapy.

Antigens known to be found on cancer, and useful for the practice of the invention include: epidermal growth factor receptor (EGFR, EGFR1, ErbB-1, HER1); ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family (IGF-1R); platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family; TRK receptor family; ephrin (EPH) receptor family; AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; transforming growth factor alpha (TGF-alpha), TGF-alphareceptor; transforming growth factor-beta (TGF-beta), TGF-beta receptor; interleukin beta receptor alpha2 chain (IL13Ralpha2); interleukin-6 (IL-6), 1L-6 receptor; interleukin-4, IL-4 receptor; cytokine receptors, Class I (hematopoietin family) and Class II (interferon/1L-10 family) receptors; tumor necrosis factor (TNF) family, TNF-alpha; tumor necrosis factor (TNF) receptor superfamily (TNTRSF); death receptor family, TRAIL-receptor; cancer-testis (CT) antigens; lineage-specific antigens; differentiation antigens; alpha-actinin-4; ARTC1, breakpoint cluster region-Abelson (Bcr-abl) fusion products; B-RAF; caspase-5 (CASP-5); caspase-8 (CASP-8); beta-catenin (CTNNB1); cell division cycle 27 (CDC27); cyclin-dependent kinase 4 (CDK4); CDKN2A; COA-1; dek-can fusion protein; EFTUD-2; Elongation factor 2 (ELF2); Ets variant gene 6/acute myeloid leukemia 1 gene ETS (ETC6-AML1) fusion protein; fibronectin (FN); GPNMB; low density lipid receptor/GDP-L fucose; beta-D-galactose 2-alpha-Lfucosyltraosferase (LDLR/FUT) fusion protein; HLA-A2; MLA-All; heat shock protein 70-2 mutated (HSP70-2M); KIAA0205; MART2; melanoma ubiquitous mutated 1, 2, 3 (MUM-1, 2, 3); prostatic acid phosphatase (PAP); neo-PAP; Myosin class 1; NFYC; OGT, OS-9; pml-RARalpha fusion protein; PRDX5; PTPRK, K-ras (KRAS2); N-ras (NRAS); HRAS; RBAF600; SIRT12; SNRPD1; SYT-SSX1 or -SSX2 fusion protein; Triosephosphate Isomerase; BAGE; BAGE-1; BAGE-2, 3, 4, 5; GAGE-1, 2, 3, 4, 5, 6, 7, 8; GnT-V (aberrant N-acetyl glucosaminyl transferase V; MGAT5), HERV-K MEL, KK-LC, KM-HN-1, LAGE, LAGE-1, CTL-recognized antigen on melanoma (CAMEL), MAGE-A1 (MAGE-1); MAGE-A2; MAGE-A3; MAGE-A4; MAGE-AS; MAGE-A6; MAGE-A8; MAGE-A9; MAGE-A10; MAGE-A11; MAGE-A12; MAGE-3; MAGE-B1; MAGE-B2; MAGE-B5; MAGE-B6; MAGE-C1; MAGE-C2; mucin 1 (MUC1); MART-1/Melan-A (MLANA); gp100; gp100/Pme117 (S1LV); tyrosinase (TYR); TRP-1; HAGE; NA-88; NY-ESO-1; NY-ESO-1/LAGE-2; SAGE, Sp17; SSX-1, 2, 3, 4; TRP2-1NT2; carcino-embryonic antigen (CEA); Kallikrein 4; mammaglobin-A; OA1; prostate specific antigen (PSA); prostate specific membrane antigen; TRP-1/, 75; TRP-2 adipophilin; interferon inducible protein absent in melanoma 2 (AIM-2); BING-4; CPSF; cyclin D1; epithelial cell adhesion molecule (Ep-CAM); EpbA3; fibroblast growth factor-5 (FGF-5); glycoprotein 250 (gp250intestinal carboxyl esterase (iCE); alpha-feto protein (AFP); M-CSF; mdm-2; MUCI; p53 (TP53); PBF; PRAME; PSMA; RAGE-1; RNF43; RU2AS; SOX10; STEAP1; survivin (BIRCS); human telomerase reverse transcriptase (hTERT); telomerase; Wilms' tumor gene (WT1); SYCP1; BRDT; SPANX; XAGE; ADAM2; PAGE-5; LIP1; CTAGE-1; CSAGE; MMA1; CAGE; BORIS; HOM-TES-85; AF15q14; HCA66I; LDHC; MORC; SGY-1; SPO11; TPX1; NY-SAR-35; FTHLI7; NXF2 TDRD1; TEX 15; FATE; TPTE; immunoglobulin idiotypes; Bence-Jones protein; estrogen receptors (ER); androgen receptors (AR); CD40; CD30; CD20; CD19; CD33; CD4; CD25; CD3; cancer antigen 72-4 (CA 72-4); cancer antigen 15-3 (CA 15-3); cancer antigen 27-29 (CA 27-29); cancer antigen 125 (CA 125); cancer antigen 19-9 (CA 19-9); beta-human chorionic gonadotropin; 1-2 microglobulin; squamous cell carcinoma antigen; neuron-specific enolase; heat shock protein gp96; GM2, sargramostim; CTLA-4; 707 alanine proline (707-AP); adenocarcinoma antigen recognized by T cells 4 (ART-4); carcinoembryogenic antigen peptide-1 (CAP-1); calcium-activated chloride channel-2 (CLCA2); cyclophilin B (Cyp-B); and human signet ring tumor-2 (HST-2).

In one embodiment, the invention teaches the use of removal of extracorporeal blocking factors to increase the number of dendritic cells infiltrating tumors. The utilization of dendritic cells as an immunotherapy is known in the art and ways of using dendritic cell therapy are defined in the following examples for melanoma [67-118], soft tissue sarcoma [119], thyroid [120-122], glioma [123-144], multiple myeloma, [145-153], lymphoma [154-156], leukemia [157-164], as well as liver [165-170], lung [171-184], ovarian [185-188], and pancreatic cancer [189-191]. In other embodiments the invention teaches the use of extracorporeal removal of immunological blocking factors for augmentation of existing dendritic cells to infiltrate tumors. Means of assessing dendritic cell infiltration are known in the art and described in the following examples: for gastric cancer [192-195], head and neck cancer [196-200], cervical cancer [201], breast cancer [202-204], lung cancer [205], colorectal cancer [206-208], liver cancer [209, 210], gall bladder cancer [211, 212], and pancreatic cancer [213].

REFERENCES

1. Mukherjee, N., K. M. Wheeler, and R. S. Svatek, *Bacillus Calmette-Guerin treatment of bladder cancer: a systematic review and commentary on recent publications.* Curr Opin Urol, 2019.
2. Lemdani, K., et al., *Local immunomodulation combined to radiofrequency ablation results in a complete cure of local and distant colorectal carcinoma.* Oncoimmunology, 2019. 8(3): p. 1550342.
3. Pettenati, C. and M. A. Ingersoll, *Mechanisms of BCG immunotherapy and its outlook for bladder cancer.* Nat Rev Urol, 2018. 15(10): p. 615-625.
4. Mukherjee, N. and R. Svatek, *Cancer Immune Therapy: Prognostic Significance and Implications for Therapy of PD-1 in BCG-Relapsing Bladder Cancer.* Ann Surg Oncol, 2018. 25(9): p. 2498-2499.
5. Godoy-Calderon, M. J., et al., *Autologous tumor cells/bacillus Calmette-Guerin/formalin-based novel breast cancer vaccine induces an immune antitumor response.* Oncotarget, 2018. 9(29): p. 20222-20238.
6. Davis, R. L., 3rd, W. Le, and Z. Cui, *Granulocytes as an effector mechanism of BCG therapy for bladder cancer.* Med Hypotheses, 2017. 104: p. 166-169.
7. Morales, A., *BCG: A throwback from the stone age of vaccines opened the path for bladder cancer immunotherapy.* Can J Urol, 2017. 24(3): p. 8788-8793.
8. Kowalewicz-Kulbat, M. and C. Locht, *BCG and protection against inflammatory and auto-immune diseases.* Expert Rev Vaccines, 2017. 16(7): p. 1-10.
9. Prack Mc Cormick, B., et al., *Bacillus Calmette-Guerin improves local and systemic response to radiotherapy in invasive bladder cancer.* Nitric Oxide, 2017. 64: p. 22-30.
10. Pichler, R., et al., *Tumor-infiltrating immune cell subpopulations influence the oncologic outcome after intravesical Bacillus Calmette-Guerin therapy in bladder cancer.* Oncotarget, 2016. 7(26): p. 39916-39930.
11. Pan, K., et al., *OK-432 synergizes with IFN-gamma to confer dendritic cells with enhanced antitumor immunity.* Immunol Cell Biol, 2014. 92(3): p. 263-74.
12. Ohe, G., et al., *Effect of soluble factors derived from oral cancer cells on the production of interferon-gamma from peripheral blood mononuclear cells following stimulation with OK-432.* Oncol Rep, 2013. 30(2): p. 945-51.
13. Hirayama, M., et al., *Overcoming regulatory T-cell suppression by a lyophilized preparation of Streptococcus pyogenes.* Eur J Immunol, 2013. 43(4): p. 989-1000.
14. Chen, U., et al., *Vaccination with OK-432 followed by TC-1 tumor lysate leads to significant antitumor effects.* Reprod Sci, 2011. 18(7): p. 687-94.
15. Oshikawa, T., et al., *Antitumor effect of OK-432-derived DNA: one of the active constituents of OK-432, a streptococcal immunotherapeutic agent.* J Immunother, 2006. 29(2): p. 143-50.
16. Okamoto, M., et al., *Mechanism of anticancer host response induced by OK-432, a streptococcal preparation, mediated by phagocytosis and Toll-like receptor 4 signaling.* J Immunother, 2006. 29(1): p. 78-86.
17. Kimura, T., et al., *Final report of a randomized controlled study with streptococcal preparation OK-432 as a supplementary immunopotentiator for laryngeal cancer.* Acta Otolaryngol Suppl, 1996. 525: p. 135-41.
18. Ozaki, S., et al., *Mechanism of tumoricidal activity of OK-432-specific L3T4+ Lyt2− T-cells.* Cancer Res, 1990. 50(15): p. 4630-4.
19. Abe, Y., et al., *The endogenous induction of tumor necrosis factor serum (TNS) for the adjuvant postoperative immunotherapy of cancer—changes in immunological markers of the blood.* Jpn J Surg, 1990. 20(1): p. 19-26.
20. Nio, Y., et al., *Cytotoxic and cytostatic effects of the streptococcal preparation OK-432 and its subcellular fractions on human ovarian tumor cells.* Cancer, 1989. 64(2): p. 434-41.
21. Hanaue, H., et al., *Hemolytic streptococcus preparation OK-432; beneficial adjuvant therapy in recurrent gastric carcinoma.* Tokai J Exp Clin Med, 1987. 12(4): p. 209-14.
22. Ujiie, T., *OK-432-mediated augmentation of antitumor immunity and generation of cytotoxic T lymphocytes.* Jpn J Exp Med, 1987. 57(2): p. 103-15.
23. Bonavida, B., J. Katz, and T. Hoshino, *Mechanism of NK activation by OK-432 (Streptococcus pyogenes). I. Spontaneous release of NKCF and augmentation of NKCF production following stimulation with NK target cells.* Cell Immunol, 1986. 102(1): p. 126-35.

24. Uchida, A., *Augmentation of autologous tumor killing activity of tumor-associated large granular lymphocytes by the streptococcal preparation OK432.* Methods Find Exp Clin Pharmacol, 1986. 8(2): p. 81-4.
25. Toge, T., et al., *Effects of intraperitoneal administration of OK-432 for patients with advanced cancer.* Jpn J Surg, 1985. 15(4): p. 260-5.
26. Sakai, S., et al., *Studies on the properties of a streptococcal preparation OK-432 (NSC-B116209) as an immunopotentiator. I. Activation of serum complement components and peritoneal exudate cells by group A streptococcus.* Jpn J Exp Med, 1976. 46(2): p. 123-33.
27. Pampena, M. B., et al., *Dissecting the Immune Stimulation Promoted by CSF-470 Vaccine Plus Adjuvants in Cutaneous Melanoma Patients: Long Term Antitumor Immunity and Short Term Release of Acute Inflammatory Reactants.* Front Immunol, 2018. 9: p. 2531.
28. Pampena, M. B., et al., *Early Events of the Reaction Elicited by CSF-470 Melanoma Vaccine Plus Adjuvants: An In Vitro Analysis of Immune Recruitment and Cytokine Release.* Front Immunol, 2017. 8: p. 1342.
29. Lutsiak, M. E., et al., *Inhibition of CD4(+)25+ T regulatory cell function implicated in enhanced immune response by low-dose cyclophosphamide.* Blood, 2005. 105(7): p. 2862-8.
30. Beyer, M., et al., *Reduced frequencies and suppressive function of CD4+CD25hi regulatory T cells in patients with chronic lymphocytic leukemia after therapy with fludarabine.* Blood, 2005. 106(6): p. 2018-25.
31. Brode, S., et al., *Cyclophosphamide-induced type-1 diabetes in the NOD mouse is associated with a reduction of CD4+CD25+Foxp3+ regulatory T cells.* J Immunol, 2006. 177(10): p. 6603-12.
32. Salem, M. L., et al., *Defining the ability of cyclophosphamide preconditioning to enhance the antigen-specific CD8+ T-cell response to peptide vaccination: creation of a beneficial host microenvironment involving type I IFNs and myeloid cells.* J Immunother, 2007. 30(1): p. 40-53.
33. Liu, J. Y., et al., *Single administration of low dose cyclophosphamide augments the antitumor effect of dendritic cell vaccine.* Cancer Immunol Immunother, 2007. 56(10): p. 1597-604.
34. van der Most, R. G., et al., *Tumor eradication after cyclophosphamide depends on concurrent depletion of regulatory T cells: a role for cycling TNFR2-expressing effector-suppressor T cells in limiting effective chemotherapy.* Cancer Immunol Immunother, 2009. 58(8): p. 1219-28.
35. Greten, T. F., et al., *Low-dose cyclophosphamide treatment impairs regulatory T cells and unmasks AFP-specific CD4+ T-cell responses in patients with advanced HCC.* J Immunother, 2010. 33(2): p. 211-8.
36. Zhao, J., et al., *Selective depletion of CD4+CD25+Foxp3+ regulatory T cells by low-dose cyclophosphamide is explained by reduced intracellular ATP levels.* Cancer Res, 2010. 70(12): p. 4850-8.
37. Vermeij, R., et al., *Potentiation of a p53-SLP vaccine by cyclophosphamide in ovarian cancer: a single-arm phase II study.* Int J Cancer, 2012. 131(5): p. E670-80.
38. Xia, Q., et al., *Cyclophosphamide enhances anti-tumor effects of a fibroblast activation protein alpha-based DNA vaccine in tumor-bearing mice with murine breast carcinoma.* Immunopharmacol Immunotoxicol, 2017. 39(1): p. 37-44.
39. Noordam, L., et al., *Low-dose cyclophosphamide depletes circulating naive and activated regulatory T cells in malignant pleural mesothelioma patients synergistically treated with dendritic cell-based immunotherapy.* Oncoimmunology, 2018. 7(12): p. e1474318.
40. Lieberman, R., J. Wybran, and W. Epstein, *The immunologic and histopathologic changes of BCG-mediated tumor regression in patients with malignant melanoma.* Cancer, 1975. 35(3): p. 756-77.
41. Leach, D. R., M. F. Krummel, and J. P. Allison, *Enhancement of antitumor immunity by CTLA-4 blockade.* Science, 1996. 271(5256): p. 1734-6.
42. Zhang, D., et al., *Scoring System for Tumor-Infiltrating Lymphocytes and Its Prognostic Value for Gastric Cancer.* Front Immunol, 2019. 10: p. 71.
43. Huang, J., et al., *Changes of Tumor Infiltrating Lymphocytes after Core Needle Biopsy and the Prognostic Implications in Early Stage Breast Cancer: A Retrospective Study.* Cancer Res Treat, 2019.
44. Miyoshi, Y., et al., *Associations in tumor infiltrating lymphocytes between clinicopathological factors and clinical outcomes in estrogen receptor-positive/human epidermal growth factor receptor type 2 negative breast cancer.* Oncol Lett, 2019. 17(2): p. 2177-2186.
45. Loi, S., et al., *Tumor-Infiltrating Lymphocytes and Prognosis: A Pooled Individual Patient Analysis of Early-Stage Triple-Negative Breast Cancers.* J Clin Oncol, 2019. 37(7): p. 559-569.
46. Sonderstrup, I. M. H., et al., *Evaluation of tumor-infiltrating lymphocytes and association with prognosis in BRCA-mutated breast cancer.* Acta Oncol, 2019: p. 1-8.
47. Wong, P. F., et al., *Multiplex Quantitative Analysis of Tumor-Infiltrating Lymphocytes and Immunotherapy Outcome in Metastatic Melanoma.* Clin Cancer Res, 2019.
48. Shimizu, S., et al., *Tumor-infiltrating CD8(+) T-cell density is an independent prognostic marker for oral squamous cell carcinoma.* Cancer Med, 2019. 8(1): p. 80-93.
49. Bennett, J. A., V. S. Rao, and M. S. Mitchell, *Systemic bacillus Calmette-Guerin (BCG) activates natural suppressor cells.* Proc Natl Acad Sci USA, 1978. 75(10): p. 5142-4.
50. Bennett, J. A. and J. C. Marsh, *Relationship of Bacillus Calmette-Guerin-induced suppressor cells to hematopoietic precursor cells.* Cancer Res, 1980. 40(1): p. 80-5.
51. Strober, S., *Natural suppressor (NS) cells, neonatal tolerance, and total lymphoid irradiation: exploring obscure relationships.* Annu Rev Immunol, 1984. 2: p. 219-37.
52. Schwadron, R. B., D. M. Gandour, and S. Strober, *Cloned natural suppressor cell lines derived from the spleens of neonatal mice.* J Exp Med, 1985. 162(1): p. 297-310.
53. Noga, S. J., et al., *Characterization of the natural suppressor cell population in adult rat bone marrow.* J Leukoc Biol, 1988. 43(3): p. 279-87.
54. Sugiura, K., et al., *Enrichment of natural suppressor activity in a wheat germ agglutinin positive hematopoietic progenitor-enriched fraction of monkey bone marrow.* Blood, 1990. 75(5): p. 1125-31.
55. Sugiura, K., et al., *Enrichment of murine bone marrow natural suppressor activity in the fraction of hematopoietic progenitors with interleukin 3 receptor-associated antigen.* Exp Hematol, 1992. 20(2): p. 256-63.
56. Clark, D. A., et al., *Decidua-associated suppressor cells in abortion-prone DBA/2-mated CBA/J mice that release bioactive transforming growth factor beta2-related immunosuppressive molecules express a bone marrow-derived natural suppressor cell marker and gamma delta T-cell receptor.* Biol Reprod, 1997. 56(5): p. 1351-60.

57. Gronvik, K. O., D. W. Hoskin, and R. A. Murgita, *Monoclonal antibodies against murine neonatal and pregnancy-associated natural suppressor cells induce resorption of the fetus.* Scand J Immunol, 1987. 25(5): p. 533-40.
58. Subiza, J. L., et al., *Development of splenic natural suppressor (NS) cells in Ehrlich tumor-bearing mice.* Int J Cancer, 1989. 44(2): p. 307-14.
59. Vinuela, J. E., et al., *Antigen shedding vs. development of natural suppressor cells as mechanism of tumor escape in mice bearing Ehrlich tumor.* Int J Cancer, 1991. 47(1): p. 86-91.
60. Hayamizu, K., et al., *Induction of natural suppressor-like cells from human adult peripheral blood lymphocytes by a K562-derived factor.* Transplantation, 1993. 55(6): p. 1403-8.
61. Prechel, M. M., et al., *Immune modulation by interleukin-12 in tumor-bearing mice receiving vitamin D3 treatments to block induction of immunosuppressive granulocyte/macrophage progenitor cells.* Cancer Immunol Immunother, 1996. 42(4): p. 213-20.
62. Young, M. R., et al., *Increased recurrence and metastasis in patients whose primary head and neck squamous cell carcinomas secreted granulocyte-macrophage colony-stimulating factor and contained CD34+ natural suppressor cells.* Int J Cancer, 1997. 74(1): p. 69-74.
63. Wright, M. A., et al., *Stimulation of immune suppressive CD34+ cells from normal bone marrow by Lewis lung carcinoma tumors.* Cancer Immunol Immunother, 1998. 46(5): p. 253-60.
64. Martino, A., et al., *Mycobacterium bovis bacillus Calmette-Guerin vaccination mobilizes innate myeloid-derived suppressor cells restraining in vivo T cell priming via IL-1R-dependent nitric oxide production.* J Immunol, 2010. 184(4): p. 2038-47.
65. Wiers, K., et al., *Failure of tumor-reactive lymph node cells to kill tumor in the presence of immune-suppressive CD34+ cells can be overcome with vitamin D3 treatment to diminish CD34+ cell levels.* Clin Exp Metastasis, 1998. 16(3): p. 275-82.
66. Wiers, K. M., et al., *Vitamin D3 treatment to diminish the levels of immune suppressive CD34+ cells increases the effectiveness of adoptive immunotherapy.* J Immunother, 2000. 23(1): p. 115-24.
67. Nestle, F. O., et al., *Vaccination of melanoma patients with peptide- or tumor lysate-pulsed dendritic cells.* Nat Med, 1998. 4(3): p. 328-32.
68. Chakraborty, N. G., et al., *Immunization with a tumor-cell-lysate-loaded autologous-antigen-presenting-cell-based vaccine in melanoma.* Cancer Immunol Immunother, 1998. 47(1): p. 58-64.
69. Wang, F., et al., *Phase I trial of a MART-1 peptide vaccine with incomplete Freund's adjuvant for resected high-risk melanoma.* Clin Cancer Res, 1999. 5(10): p. 2756-65.
70. Thurner, B., et al., *Vaccination with mage-3A1 peptide pulsed mature, monocyte-derived dendritic cells expands specific cytotoxic T cells and induces regression of some metastases in advanced stage IV melanoma.* J Exp Med, 1999. 190(11): p. 1669-78.
71. Thomas, R., et al., *Immature human monocyte-derived dendritic cells migrate rapidly to draining lymph nodes after intradermal injection for melanoma immunotherapy.* Melanoma Res, 1999. 9(5): p. 474-81.
72. Mackensen, A., et al., *Phase I study in melanoma patients of a vaccine with peptide pulsed dendritic cells generated in vitro from CD34(+) hematopoietic progenitor cells.* Int J Cancer, 2000. 86(3): p. 385-92.
73. Panelli, M. C., et al., *Phase 1 study in patients with metastatic melanoma of immunization with dendritic cells presenting epitopes derived from the melanoma-associated antigens MART-1 and gp100.* J Immunother, 2000. 23(4): p. 487-98.
74. Schuler-Thurner, B., et al., *Mage-3 and influenza-matrix peptide-specific cytotoxic T cells are inducible in terminal stage HLA-A2.1+ melanoma patients by mature monocyte-derived dendritic cells.* J Immunol, 2000. 165(6): p. 3492-6.
75. Lau, R., et al., *Phase I trial of intravenous peptide-pulsed dendritic cells in patients with metastatic melanoma.* J Immunother, 2001. 24(1): p. 66-78.
76. Banchereau, J., et al., *Immune and clinical responses in patients with metastatic melanoma to CD34(+) progenitor-derived dendritic cell vaccine.* Cancer Res, 2001. 61(17): p. 6451-8.
77. Schuler-Thurner, B., et al., *Rapid induction of tumor-specific type 1 T helper cells in metastatic melanoma patients by vaccination with mature, cryopreserved, peptide-loaded monocyte-derived dendritic cells.* J Exp Med, 2002. 195(10): p. 1279-88.
78. Palucka, A. K., et al., *Single injection of CD34+ progenitor-derived dendritic cell vaccine can lead to induction of T-cell immunity in patients with stage IV melanoma.* J Immunother, 2003. 26(5): p. 432-9.
79. Bedrosian, I., et al., *Intranodal administration of peptide pulsed mature dendritic cell vaccines results in superior CD8+ T-cell function in melanoma patients.* J Clin Oncol, 2003. 21(20): p. 3826-35.
80. Slingluff, C. L., Jr., et al., *Clinical and immunologic results of a randomized phase II trial of vaccination using four melanoma peptides either administered in granulocyte-macrophage colony-stimulating factor in adjuvant or pulsed on dendritic cells.* J Clin Oncol, 2003. 21(21): p. 4016-26.
81. Hersey, P., et al., *Phase I/II study of treatment with dendritic cell vaccines in patients with disseminated melanoma.* Cancer Immunol Immunother, 2004. 53(2): p. 125-34.
82. Vilella, R., et al., *Pilot study of treatment of biochemotherapy-refractory stage IV melanoma patients with autologous dendritic cells pulsed with a heterologous melanoma cell line lysate.* Cancer Immunol Immunother, 2004. 53(7): p. 651-8.
83. Palucka, A. K., et al., *Spontaneous proliferation and type 2 cytokine secretion by CD4+T cells in patients with metastatic melanoma vaccinated with antigen-pulsed dendritic cells.* J Clin Immunol, 2005. 25(3): p. 288-95.
84. Banchereau, J., et al., *Immune and clinical outcomes in patients with stage IV melanoma vaccinated with peptide-pulsed dendritic cells derived from CD34+ progenitors and activated with type I interferon.* J Immunother, 2005. 28(5): p. 505-16.
85. Trakatelli, M., et al., *A new dendritic cell vaccine generated with interleukin-3 and interferon-beta induces CD8+ T cell responses against NA17-A2 tumor peptide in melanoma patients.* Cancer Immunol Immunother, 2006. 55(4): p. 469-74.
86. Salcedo, M., et al., *Vaccination of melanoma patients using dendritic cells loaded with an allogeneic tumor cell lysate.* Cancer Immunol Immunother, 2006. 55(7): p. 819-29.
87. Linette, G. P., et al., *Immunization using autologous dendritic cells pulsed with the melanoma-associated anti-* gen *gp*100-*derived G*280-9V peptide elicits CD8+ *immunity.* Clin Cancer Res, 2005. 11(21): p. 7692-9.

88. Escobar, A., et al., *Dendritic cell immunizations alone or combined with low doses of interleukin-2 induce specific immune responses in melanoma patients.* Clin Exp Immunol, 2005. 142(3): p. 555-68.

89. Tuettenberg, A., et al., *Induction of strong and persistent MelanA/MART-1-specific immune responses by adjuvant dendritic cell-based vaccination of stage II melanoma patients.* Int J Cancer, 2006. 118(10): p. 2617-27.

90. Schadendorf, D., et al., *Dacarbazine (DTIC) versus vaccination with autologous peptide pulsed dendritic cells (DC) in first-line treatment of patients with metastatic melanoma: a randomized phase III trial of the DC study group of the DeCOG.* Ann Oncol, 2006. 17(4): p. 563-70.

91. Di Pucchio, T., et al., *Immunization of stage IV melanoma patients with Melan-A/MART-1 and gp100 peptides plus IFN-alpha results in the activation of specific CD8(+) T cells and monocyte/dendritic cell precursors.* Cancer Res, 2006. 66(9): p. 4943-51.

92. Nakai, N., et al., *Vaccination of Japanese patients with advanced melanoma with peptide, tumor lysate or both peptide and tumor lysate pulsed mature, monocyte-derived dendritic cells.* J Dermatol, 2006. 33(7): p. 462-72.

93. Palucka, A. K., et al., *Dendritic cells loaded with killed allogeneic melanoma cells can induce objective clinical responses and MART-1 specific CD8+ T-cell immunity.* J Immunother, 2006. 29(5): p. 545-57.

94. Lesimple, T., et al., *Immunologic and clinical effects of injecting mature peptide-loaded dendritic cells by intralymphatic and intranodal routes in metastatic melanoma patients.* Clin Cancer Res, 2006. 12(24): p. 7380-8.

95. Guo, J., et al., *Intratumoral injection of dendritic cells in combination with local hyperthermia induces systemic antitumor effect in patients with advanced melanoma.* Int J Cancer, 2007. 120(11): p. 2418-25.

96. O'Rourke, M. G., et al., *Dendritic cell immunotherapy for stage IV melanoma.* Melanoma Res, 2007. 17(5): p. 316-22.

97. Bercovici, N., et al., *Analysis and characterization of antitumor T-cell response after administration of dendritic cells loaded with allogeneic tumor lysate to metastatic melanoma patients.* J Immunother, 2008. 31(1): p. 101-12.

98. Hersey, P., et al., *Phase I/II study of treatment with matured dendritic cells with or without low dose IL-2 in patients with disseminated melanoma.* Cancer Immunol Immunother, 2008. 57(7): p. 1039-51.

99. von Euw, E. M., et al., *A phase I clinical study of vaccination of melanoma patients with dendritic cells loaded with allogeneic apoptotic/necrotic melanoma cells. Analysis of toxicity and immune response to the vaccine and of IL-10 -1082 promoter genotype as predictor of disease progression.* J Transl Med, 2008. 6: p. 6.

100. Carrasco, J., et al., *Vaccination of a melanoma patient with mature dendritic cells pulsed with MAGE-3 peptides triggers the activity of nonvaccine anti-tumor cells.* J Immunol, 2008. 180(5): p. 3585-93.

101. Redman, B. G., et al., *Phase Ib trial assessing autologous, tumor-pulsed dendritic cells as a vaccine administered with or without IL-2 in patients with metastatic melanoma.* J Immunother, 2008. 31(6): p. 591-8.

102. Daud, A. I., et al., *Phenotypic and functional analysis of dendritic cells and clinical outcome in patients with high-risk melanoma treated with adjuvant granulocyte macrophage colony-stimulating factor.* J Clin Oncol, 2008. 26(19): p. 3235-41.

103. Engell-Noerregaard, L., et al., *Review of clinical studies on dendritic cell-based vaccination of patients with malignant melanoma: assessment of correlation between clinical response and vaccine parameters.* Cancer Immunol Immunother, 2009. 58(1): p. 1-14.

104. Nakai, N., et al., *Immunohistological analysis of peptide-induced delayed-type hypersensitivity in advanced melanoma patients treated with melanoma antigen-pulsed mature monocyte-derived dendritic cell vaccination.* J Dermatol Sci, 2009. 53(1): p. 40-7.

105. Dillman, R. O., et al., *Phase II trial of dendritic cells loaded with antigens from self-renewing, proliferating autologous tumor cells as patient-specific antitumor vaccines in patients with metastatic melanoma: final report.* Cancer Biother Radiopharm, 2009. 24(3): p. 311-9.

106. Chang, J. W., et al., *Immunotherapy with dendritic cells pulsed by autologous dactinomycin-induced melanoma apoptotic bodies for patients with malignant melanoma.* Melanoma Res, 2009. 19(5): p. 309-15.

107. Trepiakas, R., et al., *Vaccination with autologous dendritic cells pulsed with multiple tumor antigens for treatment of patients with malignant melanoma: results from a phase I/II trial.* Cytotherapy, 2010. 12(6): p. 721-34.

108. Jacobs, J. F., et al., *Dendritic cell vaccination in combination with anti-CD25 monoclonal antibody treatment: a phase I/II study in metastatic melanoma patients.* Clin Cancer Res, 2010. 16(20): p. 5067-78.

109. Ribas, A., et al., *Multicenter phase II study of matured dendritic cells pulsed with melanoma cell line lysates in patients with advanced melanoma.* J Transl Med, 2010. 8: p. 89.

110. Ridolfi, L., et al., *Unexpected high response rate to traditional therapy after dendritic cell-based vaccine in advanced melanoma: update of clinical outcome and subgroup analysis.* Clin Dev Immunol, 2010. 2010: p. 504979.

111. Cornforth, A. N., et al., *Resistance to the proapoptotic effects of interferon-gamma on melanoma cells used in patient-specific dendritic cell immunotherapy is associated with improved overall survival.* Cancer Immunol Immunother, 2011. 60(1): p. 123-31.

112. Lesterhuis, W. J., et al., *Wild-type and modified gp100 peptide-pulsed dendritic cell vaccination of advanced melanoma patients can lead to long-term clinical responses independent of the peptide used.* Cancer Immunol Immunother, 2011. 60(2): p. 249-60.

113. Bjoern, J., et al., *Changes in peripheral blood level of regulatory T cells in patients with malignant melanoma during treatment with dendritic cell vaccination and low-dose IL-2.* Scand J Immunol, 2011. 73(3): p. 222-33.

114. Steele, J. C., et al., *Phase I/II trial of a dendritic cell vaccine transfected with DNA encoding melan A and gp100 for patients with metastatic melanoma.* Gene Ther, 2011. 18(6): p. 584-93.

115. Kim, D. S., et al., *Immunotherapy of malignant melanoma with tumor lysate-pulsed autologous monocyte-derived dendritic cells.* Yonsei Med J, 2011. 52(6): p. 990-8.

116. Ellebaek, E., et al., *Metastatic melanoma patients treated with dendritic cell vaccination, Interleukin-2 and metronomic cyclophosphamide: results from a phase II trial.* Cancer Immunol Immunother, 2012. 61(10): p. 1791-804.

117. Dillman, R. O., et al., *Tumor stem cell antigens as consolidative active specific immunotherapy: a randomized phase II trial of dendritic cells versus tumor cells in patients with metastatic melanoma.* J Immunother, 2012. 35(8): p. 641-9.

118. Dannull, J., et al., *Melanoma immunotherapy using mature DCs expressing the constitutive proteasome.* J Clin Invest, 2013. 123(7): p. 3135-45.

119. Finkelstein, S. E., et al., *Combination of external beam radiotherapy (EBRT) with intratumoral injection of dendritic cells as neo-adjuvant treatment of high-risk soft tissue sarcoma patients.* Int J Radiat Oncol Biol Phys, 2012. 82(2): p. 924-32.

120. Stift, A., et al., *Dendritic cell vaccination in medullary thyroid carcinoma.* Clin Cancer Res, 2004. 10(9): p. 2944-53.

121. Kuwabara, K., et al., *Results of a phase I clinical study using dendritic cell vaccinations for thyroid cancer.* Thyroid, 2007. 17(1): p. 53-8.

122. Bachleitner-Hofmann, T., et al., *Pilot trial of autologous dendritic cells loaded with tumor lysate(s) from allogeneic tumor cell lines in patients with metastatic medullary thyroid carcinoma.* Oncol Rep, 2009. 21(6): p. 1585-92.

123. Yu, J. S., et al., *Vaccination of malignant glioma patients with peptide pulsed dendritic cells elicits systemic cytotoxicity and intracranial T-cell infiltration.* Cancer Res, 2001. 61(3): p. 842-7.

124. Yamanaka, R., et al., *Vaccination of recurrent glioma patients with tumour lysate-pulsed dendritic cells elicits immune responses: results of a clinical phase I/II trial.* Br J Cancer, 2003. 89(7): p. 1172-9.

125. Yu, J. S., et al., *Vaccination with tumor lysate pulsed dendritic cells elicits antigen-specific, cytotoxic T-cells in patients with malignant glioma.* Cancer Res, 2004. 64(14): p. 4973-9.

126. Yamanaka, R., et al., *Tumor lysate and IL-18 loaded dendritic cells elicits Th1 response, tumor-specific CD8+ cytotoxic T cells in patients with malignant glioma.* J Neurooncol, 2005. 72(2): p. 107-13.

127. Yamanaka, R., et al., *Clinical evaluation of dendritic cell vaccination for patients with recurrent glioma: results of a clinical phase I/II trial.* Clin Cancer Res, 2005. 11(11): p. 4160-7.

128. Liau, L. M., et al., *Dendritic cell vaccination in glioblastoma patients induces systemic and intracranial T-cell responses modulated by the local central nervous system tumor microenvironment.* Clin Cancer Res, 2005. 11(15): p. 5515-25.

129. Walker, D. G., et al., *Results of a phase I dendritic cell vaccine trial for malignant astrocytoma: potential interaction with adjuvant chemotherapy.* J Clin Neurosci, 2008. 15(2): p. 114-21.

130. Leplina, O. Y., et al., *Use of interferon-alpha-induced dendritic cells in the therapy of patients with malignant brain gliomas.* Bull Exp Biol Med, 2007. 143(4): p. 528-34.

131. De Vleeschouwer, S., et al., *Postoperative adjuvant dendritic cell-based immunotherapy in patients with relapsed glioblastoma multiforme.* Clin Cancer Res, 2008. 14(10): p. 3098-104.

132. Ardon, H., et al., *Adjuvant dendritic cell-based tumour vaccination for children with malignant brain tumours.* Pediatr Blood Cancer, 2010. 54(4): p. 519-25.

133. Prins, R. M., et al., *Gene expression profile correlates with T-cell infiltration and relative survival in glioblastoma patients vaccinated with dendritic cell immunotherapy.* Clin Cancer Res, 2011. 17(6): p. 1603-15.

134. Okada, H., et al., *Induction of CD8+ T-cell responses against novel glioma-associated antigen peptides and clinical activity by vaccinations with {alpha}-type 1 polarized dendritic cells and polyinosinic-polycytidylic acid stabilized by lysine and carboxymethylcellulose in patients with recurrent malignant glioma.* J Clin Oncol, 2011. 29(3): p. 330-6.

135. Fadul, C. E., et al., *Immune response in patients with newly diagnosed glioblastoma multiforme treated with intranodal autologous tumor lysate-dendritic cell vaccination after radiation chemotherapy.* J Immunother, 2011. 34(4): p. 382-9.

136. Chang, C. N., et al., *A phase I/II clinical trial investigating the adverse and therapeutic effects of a postoperative autologous dendritic cell tumor vaccine in patients with malignant glioma.* J Clin Neurosci, 2011. 18(8): p. 1048-54.

137. Cho, D. Y., et al., *Adjuvant immunotherapy with whole-cell lysate dendritic cells vaccine for glioblastoma multiforme: a phase II clinical trial.* World Neurosurg, 2012. 77(5-6): p. 736-44.

138. Iwami, K., et al., *Peptide-pulsed dendritic cell vaccination targeting interleukin-13 receptor alpha2 chain in recurrent malignant glioma patients with HLA-A*24/A*02 allele.* Cytotherapy, 2012. 14(6): p. 733-42.

139. Fong, B., et al., *Monitoring of regulatory T cell frequencies and expression of CTLA-4 on T cells, before and after DC vaccination, can predict survival in GBM patients.* PLoS One, 2012. 7(4): p. e32614.

140. De Vleeschouwer, S., et al., *Stratification according to HGG-IMMUNO RPA model predicts outcome in a large group of patients with relapsed malignant glioma treated by adjuvant postoperative dendritic cell vaccination.* Cancer Immunol Immunother, 2012. 61(11): p. 2105-12.

141. Phuphanich, S., et al., *Phase I trial of a multi-epitope-pulsed dendritic cell vaccine for patients with newly diagnosed glioblastoma.* Cancer Immunol Immunother, 2013. 62(1): p. 125-35.

142. Akiyama, Y., et al., *alpha-type-1 polarized dendritic cell-based vaccination in recurrent high-grade glioma: a phase I clinical trial.* BMC Cancer, 2012. 12: p. 623.

143. Prins, R. M., et al., *Comparison of glioma-associated antigen peptide-loaded versus autologous tumor lysate-loaded dendritic cell vaccination in malignant glioma patients.* J Immunother, 2013. 36(2): p. 152-7.

144. Shah, A. H., et al., *Dendritic cell vaccine for recurrent high-grade gliomas in pediatric and adult subjects: clinical trial protocol.* Neurosurgery, 2013. 73(5): p. 863-7.

145. Reichardt, V. L., et al., *Idiotype vaccination using dendritic cells after autologous peripheral blood stem cell transplantation for multiple myeloma—a feasibility study.* Blood, 1999. 93(7): p. 2411-9.

146. Lim, S. H. and R. Bailey-Wood, *Idiotypic protein pulsed dendritic cell vaccination in multiple myeloma.* Int J Cancer, 1999. 83(2): p. 215-22.

147. Motta, M. R., et al., *Generation of dendritic cells from CD14+ monocytes positively selected by immunomagnetic adsorption for multiple myeloma patients enrolled in a clinical trial of anti-idiotype vaccination.* Br J Haematol, 2003. 121(2): p. 240-50.

148. Reichardt, V. L., et al., *Idiotype vaccination of multiple myeloma patients using monocyte-derived dendritic cells.* Haematologica, 2003. 88(10): p. 1139-49.

149. Guardino, A. E., et al., *Production of myeloid dendritic cells (DC) pulsed with tumor-specific idiotype protein for* vaccination of patients with multiple myeloma. Cytotherapy, 2006. 8(3): p. 277-89.
150. Lacy, M. Q., et al., *Idiotype-pulsed antigen presenting cells following autologous transplantation for multiple myeloma may be associated with prolonged survival.* Am J Hematol, 2009. 84(12): p. 799-802.
151. Yi, Q., et al., *Optimizing dendritic cell-based immunotherapy in multiple myeloma: intranodal injections of idiotype pulsed CD40 ligand-matured vaccines led to induction of type-1 and cytotoxic T-cell immune responses in patients.* Br J Haematol, 2010. 150(5): p. 554-64.
152. Rollig, C., et al., *Induction of cellular immune responses in patients with stage-I multiple myeloma after vaccination with autologous idiotype-pulsed dendritic cells.* J Immunother, 2011. 34(1): p. 100-6.
153. Zahradova, L., et al., *Efficacy and safety of Id-protein-loaded dendritic cell vaccine in patients with multiple myeloma—phase II study results.* Neoplasma, 2012. 59(4): p. 440-9.
154. Timmerman, J. M., et al., *Idiotype pulsed dendritic cell vaccination for B-cell lymphoma: clinical and immune responses in 35 patients.* Blood, 2002. 99(5): p. 1517-26.
155. Maier, T., et al., *Vaccination of patients with cutaneous T-cell lymphoma using intranodal injection of autologous tumor-lysate-pulsed dendritic cells.* Blood, 2003. 102(7): p. 2338-44.
156. Di Nicola, M., et al., *Vaccination with autologous tumor-loaded dendritic cells induces clinical and immunologic responses in indolent B-cell lymphoma patients with relapsed and measurable disease: a pilot study.* Blood, 2009. 113(1): p. 18-27.
157. Hus, I., et al., *Allogeneic dendritic cells pulsed with tumor lysates or apoptotic bodies as immunotherapy for patients with early-stage B-cell chronic lymphocytic leukemia.* Leukemia, 2005. 19(9): p. 1621-7.
158. Li, L., et al., *Immunotherapy for patients with acute myeloid leukemia using autologous dendritic cells generated from leukemic blasts.* Int J Oncol, 2006. 28(4): p. 855-61.
159. Roddie, H., et al., *Phase I/II study of vaccination with dendritic-like leukaemia cells for the immunotherapy of acute myeloid leukaemia.* Br J Haematol, 2006. 133(2): p. 152-7.
160. Litzow, M. R., et al., *Testing the safety of clinical-grade mature autologous myeloid DC in a phase I clinical immunotherapy trial of CML.* Cytotherapy, 2006. 8(3): p. 290-8.
161. Westermann, J., et al., *Vaccination with autologous non-irradiated dendritic cells in patients with bcr/abl+ chronic myeloid leukaemia.* Br J Haematol, 2007. 137(4): p. 297-306.
162. Hus, I., et al., *Vaccination of B-CLL patients with autologous dendritic cells can change the frequency of leukemia antigen-specific CD8+ T cells as well as CD4+CD25+FoxP3+ regulatory T cells toward an antileukemia response.* Leukemia, 2008. 22(5): p. 1007-17.
163. Palma, M., et al., *Development of a dendritic cell-based vaccine for chronic lymphocytic leukemia.* Cancer Immunol Immunother, 2008. 57(11): p. 1705-10.
164. Van Tendeloo, V. F., et al., *Induction of complete and molecular remissions in acute myeloid leukemia by Wilms' tumor 1 antigen-targeted dendritic cell vaccination.* Proc Natl Acad Sci USA, 2010. 107(31): p. 13824-9.
165. Iwashita, Y., et al., *A phase I study of autologous dendritic cell-based immunotherapy for patients with unresectable primary liver cancer.* Cancer Immunol Immunother, 2003. 52(3): p. 155-61.
166. Lee, W. C., et al., *Vaccination of advanced hepatocellular carcinoma patients with tumor lysate-pulsed dendritic cells: a clinical trial.* J Immunother, 2005. 28(5): p. 496-504.
167. Butterfield, L. H., et al., *A phase I/II trial testing immunization of hepatocellular carcinoma patients with dendritic cells pulsed with four alpha-fetoprotein peptides.* Clin Cancer Res, 2006. 12(9): p. 2817-25.
168. Palmer, D. H., et al., *A phase II study of adoptive immunotherapy using dendritic cells pulsed with tumor lysate in patients with hepatocellular carcinoma.* Hepatology, 2009. 49(1): p. 124-32.
169. El Ansary, M., et al., *Immunotherapy by autologous dendritic cell vaccine in patients with advanced HCC.* J Cancer Res Clin Oncol, 2013. 139(1): p. 39-48.
170. Tada, F., et al., *Phase I/II study of immunotherapy using tumor antigen-pulsed dendritic cells in patients with hepatocellular carcinoma.* Int J Oncol, 2012. 41(5): p. 1601-9.
171. Ueda, Y., et al., *Dendritic cell-based immunotherapy of cancer with carcinoembryonic antigen-derived, HLA-A24-restricted CTL epitope: Clinical outcomes of 18 patients with metastatic gastrointestinal or lung adenocarcinomas.* Int J Oncol, 2004. 24(4): p. 909-17.
172. Hirschowitz, E. A., et al., *Autologous dendritic cell vaccines for non-small-cell lung cancer.* J Clin Oncol, 2004. 22(14): p. 2808-15.
173. Chang, G. C., et al., *A pilot clinical trial of vaccination with dendritic cells pulsed with autologous tumor cells derived from malignant pleural effusion in patients with late-stage lung carcinoma.* Cancer, 2005. 103(4): p. 763-71.
174. Yannelli, J. R., et al., *The large scale generation of dendritic cells for the immunization of patients with non-small cell lung cancer (NSCLC).* Lung Cancer, 2005. 47(3): p. 337-50.
175. Ishikawa, A., et al., *A phase I study of alpha-galactosylceramide (KRN7000)-pulsed dendritic cells in patients with advanced and recurrent non-small cell lung cancer.* Clin Cancer Res, 2005. 11(5): p. 1910-7.
176. Antonia, S. J., et al., *Combination of p53 cancer vaccine with chemotherapy in patients with extensive stage small cell lung cancer.* Clin Cancer Res, 2006. 12(3 Pt 1): p. 878-87.
177. Perrot, I., et al., *Dendritic cells infiltrating human non-small cell lung cancer are blocked at immature stage.* J Immunol, 2007. 178(5): p. 2763-9.
178. Hirschowitz, E. A., et al., *Immunization of NSCLC patients with antigen-pulsed immature autologous dendritic cells.* Lung Cancer, 2007. 57(3): p. 365-72.
179. Baratelli, F., et al., *Pre-clinical characterization of GMP grade CCL21-gene modified dendritic cells for application in a phase I trial in non-small cell lung cancer.* J Transl Med, 2008. 6: p. 38.
180. Hegmans, J. P., et al., *Consolidative dendritic cell-based immunotherapy elicits cytotoxicity against malignant mesothelioma.* Am J Respir Crit Care Med, 2010. 181(12): p. 1383-90.
181. Urn, S. J., et al., *Phase I study of autologous dendritic cell tumor vaccine in patients with non-small cell lung cancer.* Lung Cancer, 2010. 70(2): p. 188-94.
182. Chiappori, A. A., et al., *INGN-225: a dendritic cell-based p53 vaccine (Ad.p53-DC) in small cell lung cancer: observed association between immune response and enhanced chemotherapy effect.* Expert Opin Biol Ther, 2010. 10(6): p. 983-91.

183. Perroud, M. W., Jr., et al., *Mature autologous dendritic cell vaccines in advanced non-small cell lung cancer: a phase I pilot study.* J Exp Clin Cancer Res, 2011. 30: p. 65.
184. Skachkova, O. V., et al., *Immunological markers of anti-tumor dendritic cells vaccine efficiency in patients with non-small cell lung cancer.* Exp Oncol, 2013. 35(2): p. 109-13.
185. Hernando, J. J., et al., *Vaccination with autologous tumour antigen pulsed dendritic cells in advanced gynaecological malignancies: clinical and immunological evaluation of a phase I trial.* Cancer Immunol Immunother, 2002. 51(1): p. 45-52.
186. Rahma, O. E., et al., *A gynecologic oncology group phase II trial of two p53 peptide vaccine approaches: subcutaneous injection and intravenous pulsed dendritic cells in high recurrence risk ovarian cancer patients.* Cancer Immunol Immunother, 2012. 61(3): p. 373-84.
187. Chu, C. S., et al., *Phase I/II randomized trial of dendritic cell vaccination with or without cyclophosphamide for consolidation therapy of advanced ovarian cancer in first or second remission.* Cancer Immunol Immunother, 2012. 61(5): p. 629-41.
188. Kandalaft, L. E., et al., *A Phase I vaccine trial using dendritic cells pulsed with autologous oxidized lysate for recurrent ovarian cancer.* J Transl Med, 2013. 11: p. 149.
189. Lepisto, A. J., et al., *A phase I/II study of a MUC1 peptide pulsed autologous dendritic cell vaccine as adjuvant therapy in patients with resected pancreatic and biliary tumors.* Cancer Ther, 2008. 6(B): p. 955-964.
190. Rong, Y., et al., *A phase I pilot trial of MUC1-peptide-pulsed dendritic cells in the treatment of advanced pancreatic cancer.* Clin Exp Med, 2012. 12(3): p. 173-80.
191. Endo, H., et al., *Phase I trial of preoperative intratumoral injection of immature dendritic cells and OK-432 for resectable pancreatic cancer patients.* J Hepatobiliary Pancreat Sci, 2012. 19(4): p. 465-75.
192. Tsujitani, S., et al., *Infiltration of dendritic cells in relation to tumor invasion and lymph node metastasis in human gastric cancer.* Cancer, 1990. 66(9): p. 2012-6.
193. Tsujitani, S., et al., *Postoperative adjuvant immunochemotherapy and infiltration of dendritic cells for patients with advanced gastric cancer.* Anticancer Res, 1992. 12(3): p. 645-8.
194. Kakeji, Y., et al., *Prognostic significance of tumor-host interaction in clinical gastric cancer: relationship between DNA ploidy and dendritic cell infiltration.* J Surg Oncol, 1993. 52(4): p. 207-12.
195. Ishigami, S., et al., *Prognostic value of HLA-DR expression and dendritic cell infiltration in gastric cancer.* Oncology, 1998. 55(1): p. 65-9.
196. Giannini, A., et al., *Prognostic significance of accessory cells and lymphocytes in nasopharyngeal carcinoma.* Pathol Res Pract, 1991. 187(4): p. 496-502.
197. Gallo, O., et al., *Correlations between histopathological and biological findings in nasopharyngeal carcinoma and its prognostic significance.* Laryngoscope, 1991. 101(5): p. 487-93.
198. Furihata, M., et al., *HLA-DR antigen- and S-100 protein-positive dendritic cells in esophageal squamous cell carcinoma—their distribution in relation to prognosis.* Virchows Arch B Cell Pathol Incl Mol Pathol, 1992. 61(6): p. 409-14.
199. Reichert, T. E., et al., *The number of intratumoral dendritic cells and zeta-chain expression in T cells as prognostic and survival biomarkers in patients with oral carcinoma.* Cancer, 2001. 91(11): p. 2136-47.
200. Timar, J., et al., *Neoadjuvant immunotherapy of oral squamous cell carcinoma modulates intratumoral CD4/CD8 ratio and tumor microenvironment: a multicenter phase II clinical trial.* J Clin Oncol, 2005. 23(15): p. 3421-32.
201. Nakano, T., et al., *Antitumor activity of Langerhans cells in radiation therapy for cervical cancer and its modulation with SPG administration.* In Vivo, 1993. 7(3): p. 257-63.
202. Lespagnard, L., et al., *Tumor-infiltrating dendritic cells in adenocarcinomas of the breast: a study of 143 neoplasms with a correlation to usual prognostic factors and to clinical outcome.* Int J Cancer, 1999. 84(3): p. 309-14.
203. Iwamoto, M., et al., *Prognostic value of tumor-infiltrating dendritic cells expressing CD83 in human breast carcinomas.* Int J Cancer, 2003. 104(1): p. 92-7.
204. Coventry, B. J. and J. Morton, *CD1a-positive infiltrating-dendritic cell density and 5-year survival from human breast cancer.* Br J Cancer, 2003. 89(3): p. 533-8.
205. Zhao, R., et al., *[Study on the relationship between the dendritic cell infiltration in cancer tissues and prognosis in patients with lung cancer].* Zhongguo Fei Ai Za Zhi, 2002. 5(2): p. 112-4.
206. Diederichsen, A. C., et al., *Prognostic value of the CD4+/CD8+ ratio of tumour infiltrating lymphocytes in colorectal cancer and HLA-DR expression on tumour cells.* Cancer Immunol Immunother, 2003. 52(7): p. 423-8.
207. Dadabayev, A. R., et al., *Dendritic cells in colorectal cancer correlate with other tumor-infiltrating immune cells.* Cancer Immunol Immunother, 2004. 53(11): p. 978-86.
208. Sandel, M. H., et al., *Prognostic value of tumor-infiltrating dendritic cells in colorectal cancer: role of maturation status and intratumoral localization.* Clin Cancer Res, 2005. 11(7): p. 2576-82.
209. Yin, X. Y., et al., *Prognostic significances of tumor-infiltrating S-100 positive dendritic cells and lymphocytes in patients with hepatocellular carcinoma.* Hepatogastroenterology, 2003. 50(53): p. 1281-4.
210. Cal, X. Y., et al., *Dendritic cell infiltration and prognosis of human hepatocellular carcinoma.* J Cancer Res Clin Oncol, 2006. 132(5): p. 293-301.
211. Nakakubo, Y., et al., *Clinical significance of immune cell infiltration within gallbladder cancer.* Br J Cancer, 2003. 89(9): p. 1736-42.
212. Furihata, M., et al., *Prognostic significance of CD83 positive, mature dendritic cells in the gallbladder carcinoma.* Oncol Rep, 2005. 14(2): p. 353-6.
213. Fukunaga, A., et al., *CD8+ tumor-infiltrating lymphocytes together with CD4+ tumor-infiltrating lymphocytes and dendritic cells improve the prognosis of patients with pancreatic adenocarcinoma.* Pancreas, 2004. 28(1): p. e26-31.

The invention claimed is:

1. A method of treating or ameliorating the effects of a tumor in a patient with non-small cell lung cancer (NSCLC) comprising:
   identifying a patient having a tumor;
   selecting an antibody selected from the group consisting of: an anti-PD-1 antibody and an anti-PD-L1 antibody;
   administering said antibody to said patient to treat or ameliorate the effects of said tumor; and
   extracorporeally removing soluble Tumor Necrosis Factor (TNF)-alpha receptor from said patient.

2. The method of claim 1, wherein said antibody is an anti-PD-1 antibody.

3. The method of claim 1, wherein said removal of said soluble TNF-alpha receptor is performed by affinity capture to TNF-alpha trimers.

4. The method of claim 1, wherein said removal of said soluble TNF-alpha receptor is performed using an extracorporeal affinity capture substrate comprising immobilized TNF-alpha molecules selected from the group consisting of: TNF-alpha trimers, native TNF-alpha molecules, and mutated forms of TNF-alpha, wherein said immobilized TNF-alpha molecules on the extracorporeal affinity capture substrate have at least one binding site capable of selectively binding to soluble TNF alpha receptor from a biological fluid.

5. The method of claim 1, wherein said removal of said soluble TNF-alpha receptor is performed using an apheresis system utilizing centrifugal plasma separation.

6. The method of claim 1, wherein said removal of said soluble TNF-alpha receptor is performed using an apheresis system utilizing membrane plasma separation.

7. The method of claim 1, wherein the antibody is an anti-PD-L1 antibody.

8. The method of claim 7, wherein the antibody is selected from the group consisting of: BMS-936559, durvalumab, atezolizumab, and avelumab.

9. The method of claim 2, wherein the antibody is selected from the group consisting of: nivolumab, and pembrolizumab.

10. The method of claim 2, wherein the antibody is nivolumab.

11. The method of claim 1, wherein the TNF-alpha receptor is selected from a TNF receptor superfamily (TNFRSF).

* * * * *